(12) United States Patent
Bernacki

(10) Patent No.: US 7,876,443 B2
(45) Date of Patent: Jan. 25, 2011

(54) MULTIPASS OPTICAL DEVICE AND PROCESS FOR GAS AND ANALYTE DETERMINATION

(75) Inventor: Bruce E. Bernacki, Kennewick, WA (US)

(73) Assignee: Battelle Memorial Institute, Richland, WA (US)

( * ) Notice: Subject to any disclaimer, the term of this patent is extended or adjusted under 35 U.S.C. 154(b) by 352 days.

(21) Appl. No.: 12/239,978

(22) Filed: Sep. 29, 2008

(65) Prior Publication Data
US 2010/0079760 A1      Apr. 1, 2010

(51) Int. Cl.
*G01N 21/00*      (2006.01)

(52) U.S. Cl. ...................... 356/437; 356/432

(58) Field of Classification Search ......... 356/432–440; 359/838; 250/336.1, 339.01–339.02, 339.05–339.06, 250/339.12–339.13
See application file for complete search history.

(56) References Cited

U.S. PATENT DOCUMENTS

| 3,940,711 A | 2/1976 | Casperson | |
| 2007/0279633 A1* | 12/2007 | Yi et al. | ..................... 356/432 |

OTHER PUBLICATIONS

White, J.U., Long paths of large optical aperture, JOSA, 32, 1942, pp. 285-288.
White, J.U., Very long optical paths in air, JOSA, 66, 1976, pp. 411-416.
Herriott, D., H. Kogelnik and R. Kompfner, Off-Axis Paths in Spherical Mirror Interferometers, Appl. Opt., 3, 1964, pp. 523-526.
Herriott, D.R. and H.J. Schulte, Folded Optical Delay Lines, Appl. Opt. 4, 1965, pp. 883-889.
Altmann, J.R. Baumgart and C. Weitkamp, Two-mirror multipass absorption cell, Appl. Opt., 20, 1981, pp. 995-999.
Engle, G.S., and E.J. Moyer, Precise multipass Herriott cell design: Derivation of controlling design equations, Opt. Lett., 32, 2007, pp. 704-706.
McManus, J.B., P.L. Kebabian, and M.S. Zahniser, Astigmatic mirror multipass absorption cells for long-path-length spectroscopy, Pppl. Opt., 34, 1995, pp. 3336-3348.
Tarsitano, G.G., and C.R. Webster, Multilaser Herriott cell for planetary tunable laser spectrometers, Appl. Opt., 46, 2007, pp. 6923-6935.
Tonomura, M., et al., An experimental study on a cylindrical multipass cell, CLEO/Pacific Rim 2005, Pacific Rim Conference on Lasers and Electro-Optics, 1005, pp. 1425-1426.
Munnerlyn, C.R., et al., Alignment requirements for Mode Matching in a Confocal Fabry-Perot Interferometer, Applied Optics, vol. 9, # 11, Nov. 1970, pp. 2535-2538.
Casperson, Lee W., Cylindrical laser Resonators, Journal of the Optical Society of America, vol. 63, No. 1, Jan. 1973, pp. 25-29.

* cited by examiner

*Primary Examiner*—Gregory J Toatley
*Assistant Examiner*—Tri T Ton
(74) *Attorney, Agent, or Firm*—James D. Matheson

(57) ABSTRACT

A torus multipass optical device and method are described that provide for trace level determination of gases and gas-phase analytes. The torus device includes an optical cavity defined by at least one ring mirror. The mirror delivers optical power in at least a radial and axial direction and propagates light in a multipass optical path of a predefined path length.

43 Claims, 13 Drawing Sheets

US 7,876,443 B2

MULTIPASS OPTICAL DEVICE AND PROCESS FOR GAS AND ANALYTE DETERMINATION

This invention was made with Government support under Contract DE-AC05-76RLO1830 awarded by the U.S. Department of Energy. The Government has certain rights in the invention.

FIELD OF THE INVENTION

The present invention relates generally to instrumentation and methods for gas and analyte analysis. More particularly, the invention relates to a multi-pass optical device and process for determination of gases and gas-phase analytes.

BACKGROUND OF THE INVENTION

Absorption spectroscopy is heavily used to monitor trace gases. The Herriott cell is an optical device which has proven to be a useful multipass cell design for trace gas measurement. Herriott cells typically employ two mirrors with equal radii of curvature that propagate a light beam within the cavity. It is readily constructed, is well understood, and is relatively insensitive to mirror misalignment. In such devices, multiple passes are made by the probe light in the optical cavity. In addition, the long linear optical cavity also contributes to a long path length. The Herriott cell is also suited to laser-based systems due to its ability to re-image, or refocus, a light beam as the beam traverses the optical cavity, which keeps the beam restricted within the cavity boundaries and conserves power density of the beam as it propagates within the cavity. However, the long linear cavity of a Herriott cell can provide opportunity for tenacious gas species to attach to sites along the cell wall, making purging of the cavity between measurements difficult, leading to increased measurement cycle times, especially in reduced pressure systems. Further, multi-wavelength cell designs require numerous penetrations in the end mirror with attendant mechanical interferences between the different launch and detection optics. Accordingly, new designs for gas absorption devices are needed that: 1) provide optimum path length for absorption of light in a preselected gas, 2) are easily aligned and not prone to optical misalignment, 3) minimize wall effects, and 4) provide an optical cavity capable of measuring various chemical species of interest using different wavelengths of light.

SUMMARY OF THE INVENTION

The invention in one aspect is a torus multipass optical device that provides for determination of a gas or a gas-phase analyte. The optical device includes: a torus structure that includes an optical cavity defined by at least one ring mirror. The ring mirror has optical power that propagates light introduced to the cavity in at least a radial direction and an axial direction. The propagation of light between the mirror surfaces defines a multipass propagation (optical) path of a preselected path length.

The invention also includes a method for detection of a gas or a gas-phase analyte. The method includes: introducing a gas or a gas-phase analyte into an optical device that includes a torus structure. The torus includes an optical cavity that is defined by at least one ring mirror. The ring mirror delivers optical power that propagates light introduced to the optical cavity in at least a radial direction and an axial direction and defines a multipass optical path of a predefined path length; introducing light into the optical cavity at a preselected launch angle and preselected wavelength. The gas or gas-phase analyte absorbs light at a wavelength characteristic for that gas or analyte; collecting light exiting the optical cavity at a preselected exit angle; measuring an absorption signal for the gas or the gas-phase analyte; and determining the gas or the gas-phase analyte. The method of the invention provides for determination of a preselected gas or a mixture of gases or gas-phase analytes present in a preselected gas. The optical cavity can include a single ring mirror or can include dual concentric ring mirrors, an outer ring and an inner ring. In the dual ring design, each ring faces, and is positioned apart from, the other in the cavity. This configuration also includes a central hub positioned external to the inner ring of the optical cavity at the center of the device. Mirrors of the torus optical devices have reflective surfaces that can be spherical, convex, concave, equi-concave, or astigmatic, including combinations of these reflective surfaces. In one embodiment of the dual ring design, one of the ring mirrors is a convex ring mirror and one of the ring mirrors is a concave ring mirror. In another embodiment, one of the ring mirrors is a convex ring mirror and one of the ring mirrors is a concave ring mirror. In another embodiment of the dual ring design, at least one of the ring mirrors is an astigmatic mirror or includes an astigmatic portion. In another embodiment, at least one ring mirror has a radius of curvature equal to the radius of revolution of the optical cavity. In another embodiment, at least one ring mirror has a radius of curvature different from the radius of revolution of the optical cavity. The optical device can include an open-air optical cavity or a sealed optical cavity. The sealed optical cavity can be a partially evacuated sealed cavity with a reduced pressure atmosphere or a completely evacuated cavity. In various configurations, the optical device includes at least one surface opening that allows light to enter into, and exit from, the optical cavity. In one embodiment, at least one surface opening is an off-axis opening. In another embodiment, at least one surface opening is an on-center axis opening. In other embodiments, the surface opening is located within the central torus hub. In other embodiments, the optical device includes multiple surface openings for introducing light into, or extracting light from, the optical cavity. Absorption of defined wavelengths of light in a gas of interest or an analyte in the gas introduced to the optical cavity provides for determination of a preselected gas and/or an analyte in the gas. Probe light can be of any preselected wavelength. Launch angle at which probe light is introduced into the optical cavity contributes to the path length traveled by the probe light. Light can be introduced to the optical cavity at a launch angle with respect to X- or Y-axes of from about 1 degree to about 50 degrees, respectively, depending on the radius of the ring mirror and radius of curvature of the torus in the axial direction. Light or an absorption signal exiting the cavity has an exit angle that can be determined by the selected launch angle and the radius of curvature of the selected mirror surface.

In another aspect, the invention is a system that includes a torus multipass optical device, comprising: a torus structure with an optical cavity that includes at least one ring mirror. The ring mirror propagates light in a beam introduced to the optical cavity that delivers power in at least a radial direction and an axial direction and provides a multipass optical path of a predefined path length. The system includes a light source, e.g., a laser light source. The system further includes beam steering, beam focusing, and mode-matching optics. The system also includes a lock-in amplifier and an optical detector.

In a preferred embodiment, launch of probe light is from within the boundary of a central torus hub, which is introduced to the optical cavity through an off-axis penetration in the inner ring wall. Spot patterns on the first and/or second mirrors can be extracted from the central torus hub.

The torus multipass optical (gas absorption) devices of the invention are expected to provide detection limits for trace level determination of gas and gas-phase analytes. The multipass optical devices of the invention provide path lengths of from 10 meters to greater than or equal to 1000 meters depending on the diameter of the torus and the radius of curvature of the ring mirrors. Path lengths for these devices are defined by the number of roundtrips made by light within the optical cavity. Roundtrips number from about 10 to greater than about 5,000, but are not limited thereto. Number of roundtrips depends on ring parameters and launch angles. Absorption by a gas or a gas-phase analyte of defined wavelengths of light introduced to the optical cavity provides for trace-level determination of these gases and gas-phase analytes and have detection sensitivities that range from parts-per-million to parts-per-trillion, depending on such factors as the absorption strength, laser power, cavity losses, and detector noise.

In application, the torus optical devices of the invention can be used as a gas absorption device with preselected path lengths for spectroscopy of gases and gas-phase analytes, or as components of a gas detection system or instrument. The torus optical devices of the invention can also be used as an emission stack monitor for real-time measurement of effluent gases. In other applications, the torus optical devices can be used as a gas sensor in airborne gas measurement applications, devices, or processes. In other applications, the torus optical devices can be deployed as a modular element in a multi-wavelength gas absorption spectroscopy system or process for detection of different gases and gas-phase analytes, including mixtures. For example, gases and gas-phase analytes include, but are not limited to, e.g., toxic or deadly chemicals as might be deployed in a chemical weapons attack in a gas plume, including, e.g., G-series agents such as sarin, or V-series agents such as VS, mustard gas, ricin, and phosgene. Other chemical species and analytes may also be determined. Thus, no limitations are intended. In other embodiments, a preselected number of forms optical devices can be configured as a stack or array, each device being tuned to a different wavelength that provides for multi-wavelength absorption and detection, e.g., for identification of individual gases or preselected analytes. These optical devices can also be used to determine a gas or a mixture of gases, or be configured as a component of a gas-phase analyte detection system or process. In a preferred application, stacks or arrays of two or more torus optical devices are used in the determination of two or more preselected gases or gas-phase analytes, e.g., as modular elements or components of a multi-wavelength absorption spectroscopy system or process. Alternatively, a single optical device can be coupled with a tunable laser light source to detect multiple gas-phase analytes.

DETAILED DESCRIPTION

Figure 1:
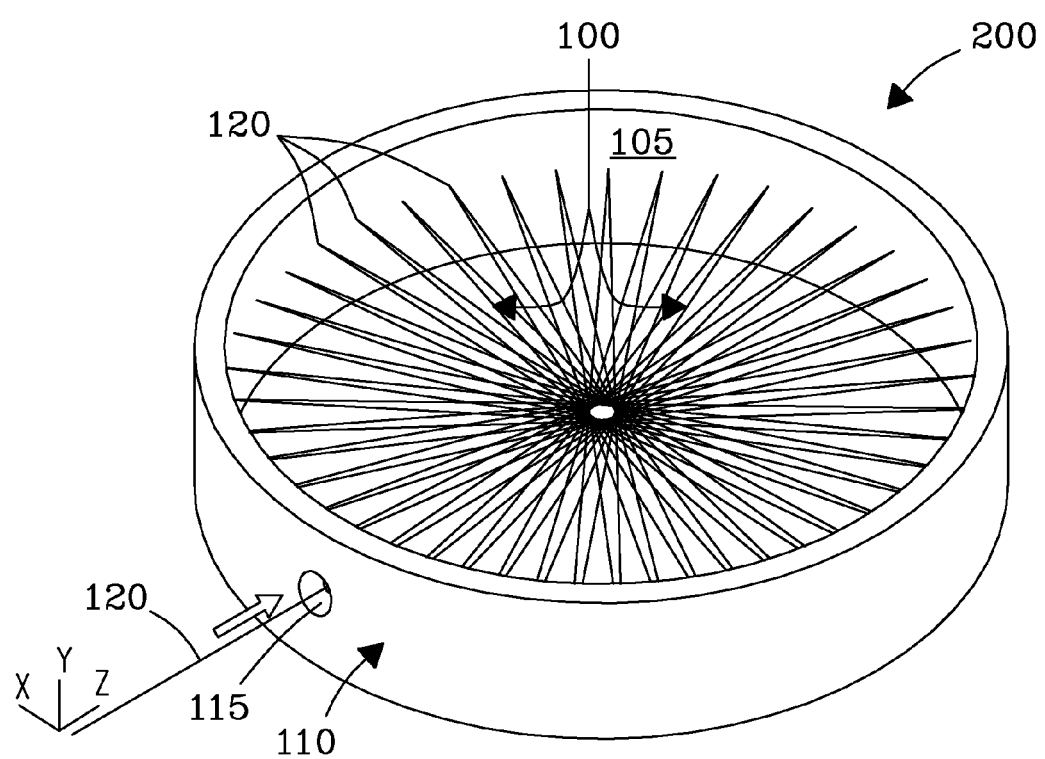
FIG. 1 illustrates a torus multipass optical device configured with a single spherical ring mirror, according to an embodiment of the invention.

The present invention in one aspect is a multipass optical device (optical cell) of a toric section design with an optical cavity defined by at least one seamless ring mirror. The term "seamless" as used herein means the surface of the ring mirror does not have seams or joints as it is not constructed by joining two or more mirror segments. The ring mirror has a surface of revolution along the circumference that is rotational symmetric with no defined optical axis that is able to propagate light introduced to the cavity in at least a radial direction and an axial direction such that it is optically continuous at all locations on the face of the ring mirror. The at least one ring mirror in the optical cavity defines a multipass optical path of a predefined path length. The preselected path length of the optical cavity provides for ultra-trace determination of gases and gas-phase analytes. A torus is a doughnut-shaped structure that has a surface of revolution (i.e., a radial surface) defined by a circle with radius of curvature (r) that is swept a distance (R) from an axis of symmetry. The radial surface can have various curvatures defined by the radius (R) used to generate the surface and radius (r) in the axial direction (i.e., direction orthogonal to the radial direction). In Cartesian coordinates, a torus, radially symmetric about the Z-axis, is defined by Equation [1]:

$$(R-\sqrt{x^2+y^2})^2+z^2=r^2 \quad [1]$$

Mirrors that define the optical cavity of the torus optical device can be spherical (e.g., convex, concave), aspherical, astigmatic, or can include combinations of spherical and/or astigmatic mirrors, e.g., convex/concave (spherical); or convex/astigmatic; or astigmatic/concave, or other mirror combinations. The term "spherical" as used herein in reference to reflective mirror surfaces means a mirror surface that has spherical curvature, e.g., convex spherical curvature or concave spherical curvature. The term "aspherical" in reference to reflective mirror surfaces means that the mirror surface deviates from spherical curvature, typically to reduce optical aberrations in light beams The term "astigmatic" in reference to reflective mirror surfaces means the mirror surface has a deviation from spherical curvature that distorts electromagnetic radiation (i.e., light rays) and prevents convergence of the light beam, which yields a distorted point pattern on the mirror surface. Astigmatic mirror surfaces have a radius of curvature that is different in two perpendicular or orthogonal planes, e.g., the X-Z plane is different from that of the Y-Z plane. No limitations are intended. In general, any type of spherical or aspherical surface can be used to generate a surface of revolution with preselected optical properties, including, e.g., refractive and reflective properties. Spherical and astigmatic mirrors produce dense Lissajous-type patterns that deliver large path lengths suitable for trace level detection and determination of gases and gas-phase analytes. Lissajous patterns or curves are defined by the system of parametric equations [2] and [3]:

$$X = A \sin(at+\delta) \quad [2]$$

$$Y = B \sin(bt) \quad [3]$$

Here, X and Y represent two independent frequencies. One frequency (X) is plotted on the X-axis and a second frequency (Y) is plotted on the Y-axis. Parameters X and Y are both periodic functions of time (t). Different patterns may be generated for different values of (n) (period shift) and (c) (phase shift). The simplest patterns are formed when (n) is a ratio of small whole numbers such as 1/2, 2/3, or 1/3. The value of (c) is usually taken as 0 or 1.57 (which is actually p/2). These values give: [x=sin(w*n*t+c) and y=sin w*t].

Mirrors that define the optical cavity of the instant invention are "self-imaging" meaning they refocus light in a propagating beam as the light reflects from mirror surface to mirror surface. Parameters of the optical cavity are routinely defined using so-called g-parameters (or quality factors) detailed, e.g., by Siegman (in Lasers, University Science Books, Mill Valley, Calif., 1986, pg. 746), incorporated herein. In other embodiments, the torus includes two ring mirrors, as described further herein. The g-parameters in a dual ring torus design are defined by Equations [4] and [5]:

$$g_1 = 1 - \frac{d}{R_1} \quad [4]$$

$$g_2 = 1 - \frac{d}{R_2} \quad [5]$$

Here, ($R_1$) and ($R_2$) are the respective radii of curvature of the two ring mirrors, and (d) is the mirror separation distance. Values for the g-parameters are selected that fall within a range of values, the so-called "stability range", in order that real and finite solutions to desired Gaussian beam parameters and spot sizes are obtained. The stability range is defined by Equation [6]:

$$0 \leq (g_1)^*(g_2) \leq 1 \quad [6]$$

For two ring mirrors with two equal radii, mirror spacing can vary from a value of (d)>0 for a practical cavity up to (d)<2R. For a torus resonator with a single ring mirror, ($g_1$) =($g_2$)=(g). The stability condition is then given by Equation [7]:

$$0 \leq g^2 \leq 1 \quad [7]$$

In general, light is injected into the torus optical device through a launch hole, surface penetration, or entry point in the torus mirror wall. The light beam circulates within the optical cavity and traces a light pattern on the mirror walls. Ultimately, the ray path satisfies conditions that permit the light to exit the cavity (also termed "reentry") through the same launch hole at an angle different from the launch angle. Difference between the launch angle and the exit angle allows the absorption signal to be extracted (measured) without use of beam-splitting elements. Equations for conventional Herriott cells that predict: 1) the shape of the spot pattern on a mirror, 2) number of round trips expected for a light ray based upon the mirror radius of curvature, the launch angle, and the mirror spacing, 3) the conditions which the ray must have in order to enter and exit the cavity, and 4) where the ray's relative absorption (wavelength) values can be measured have been described, e.g., by Herriott et al. (*Appl. Opt.*, 3, pgs. 523-526, 1964; and *Appl. Opt.*, 4, pgs. 883-889, 1965), Altman et al. (*Appl. Opt.*, 20, pgs. 995-999, 1981) and Engel et al. (*Opt. Lett.*, 32, pgs. 704-706, 2007), which references are incorporated herein. A set of mathematical equations, called a matrix formalism or mathematical matrix, can be used to determine "quality factor" parameters based on input values for a given light beam that can trace the expected ray paths along the propagation (optical) axis between the selected mirrors (the so-called paraxial regime), and to plot the location of spot patterns on a mirror. If more accurate results are desired, a non-sequential ray trace software package, such as TRACEPRO® (Lambda Research, Corp., Littleton, Mass., USA) or ZEMAX® (Zemax Development Corp., Bellevue, Wash., USA) can be used to trace expected ray paths on mirror surfaces, and to track the number of round trips. All necessary cavity parameters and dimensions can be probed exactly using exact ray tracing software, e.g., using the macro control option, without recourse to approximate paraxial assumptions, as described further herein.

Single Ring Torus Design with Single Spherical Mirror

FIG. 1 illustrates a monolithic, torus multipass optical device (gas absorption cell) 200 of a single ring mirror design, according to an embodiment of the invention. Device 200 includes an optical cavity 100 with a torus cross section, described previously herein. Optical cavity 100 is configured with a single ring mirror 105, but is not limited thereto. In the instant device, mirror 105 is a spherical (equi-concave) mirror, but is not limited thereto. A penetration (entry point or launch hole) 115 through surface 110 allows light rays 120 from a light source, e.g., a laser source (not shown), to enter into, and exit from, optical cavity 100. In the figure, a single penetration 115 is shown at the center of external surface 110, but number and position of penetrations are not limited. For example, a penetration that is at an off-axis or off-center position can increase coverage of the mirror surface by the light introduced to the optical cavity. One or more penetrations can also be used to introduce or extract light or absorption signals, as will be understood by those of skill in the art. Thus, no limitations are intended. Light rays that enter optical cavity 100 are propagated in the optical cavity from mirror 105 in both a radial direction and an axial direction. Thus, the mirrors provide optical power in at least these two directions.

The term "power" as used herein is a measure of the ability of a mirror surface to converge light rays and is defined by the reciprocal of the focal length. "Focal Length" (focal distance) is the distance from the focal point of a mirror surface to the principal point. "Focal Point" means the point (e.g., on a mirror surface) at which light rays converge or the point at which light rays appear to diverge. "Principal Point" is the intersection of a principal plane with the optical (launch) axis. "Principal Plane" refers to any one of two planes orthogonal to the optical axis that is able to re-image light rays in another plane orthogonal to the optical axis with a lateral magnification of unity. The term "Re-image" refers to the ability of a mirror surface in a first location to present (image) a light ray of equal intensity at a second mirror surface in a second location (axis, direction, or plane). Light rays 120 traverse optical cavity 100 in a multipass optical pathway that provides a corresponding cumulative path length suitable for trace analysis of gases and gas-phase analytes. Optical device 200 may be configured with an optical cavity that is, e.g., open to air (i.e., an open-air), or, e.g., sealed and partially or fully evacuated. Each configuration has a suitable application. Sealed torus devices with reduced pressure, or evacuated, environments can be used when desired absorption spectra or features of a gas or analyte of interest could be obscured by collisional broadening at atmospheric pressure. Open-air torus devices can be used when pressure broadening and interferences are not expected. In the instant device, when the radius of the cavity equals the mirror radius in the axial (orthogonal) direction, light introduced to the optical cavity produces spot patterns that lie along a common circumference. For example, a mirror with 0.25 m radius of curvature revolved about a central axis at a radius of 0.25 m provides approximately 88 round trips in the cavity when light is launched at 4 degrees with respect to the Y-axis, for a path length of approximately 44 m, but is not limited thereto. The multipass optical devices described herein are self-imaging meaning they re-focus light rays in a propagating light beam as the light rays reflect from mirror surface to mirror surface. The envelope of rays that trace out a pattern on the wall around the circumference of the cell with equal spherical surface figures lie in a plane. For example, if an input ray is launched using compound Euler angles with respect to the local coordinate system's X- and Y-axes, all rays still remain in the plane, but the plane of the rays is tilted due to the launch angle with reference to the X-axis. The effect of the input ray having an angle with respect to the X-axis in addition to tilt of the pattern is to effectively change the spacing between the mirror surfaces, making additional cavity modes possible and altering the number of possible round trips and instrument's absorption path length.

Figure 2A:
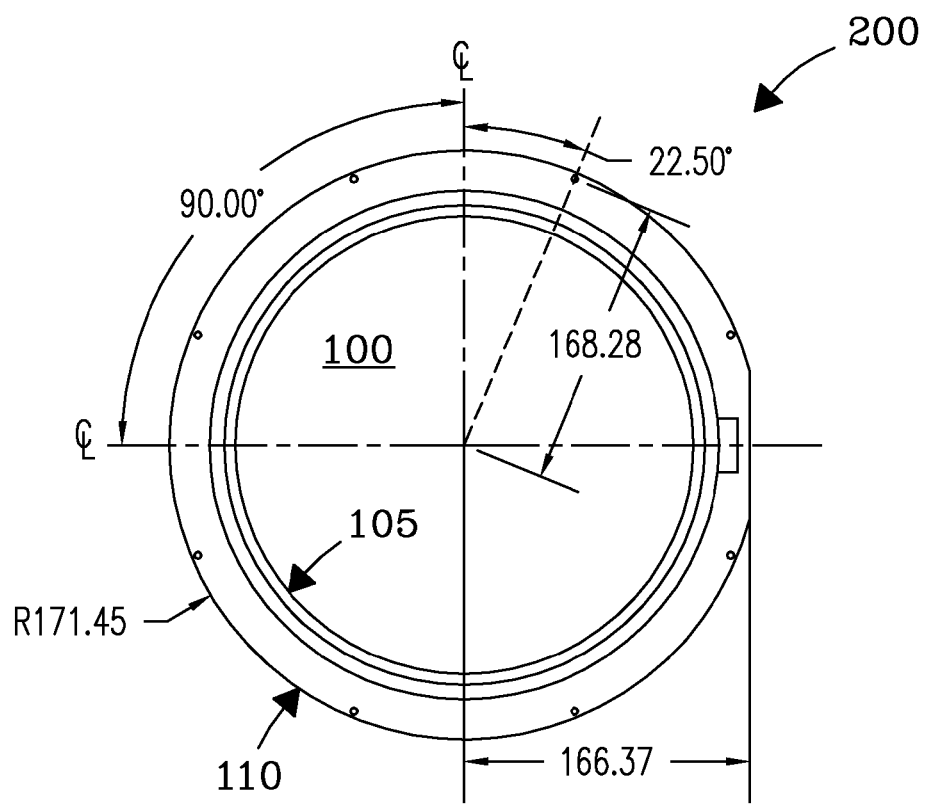
FIG. 2a is a schematic showing an on-end view of the torus optical device of FIG. 1 with exemplary dimensions.
Figure 2B:
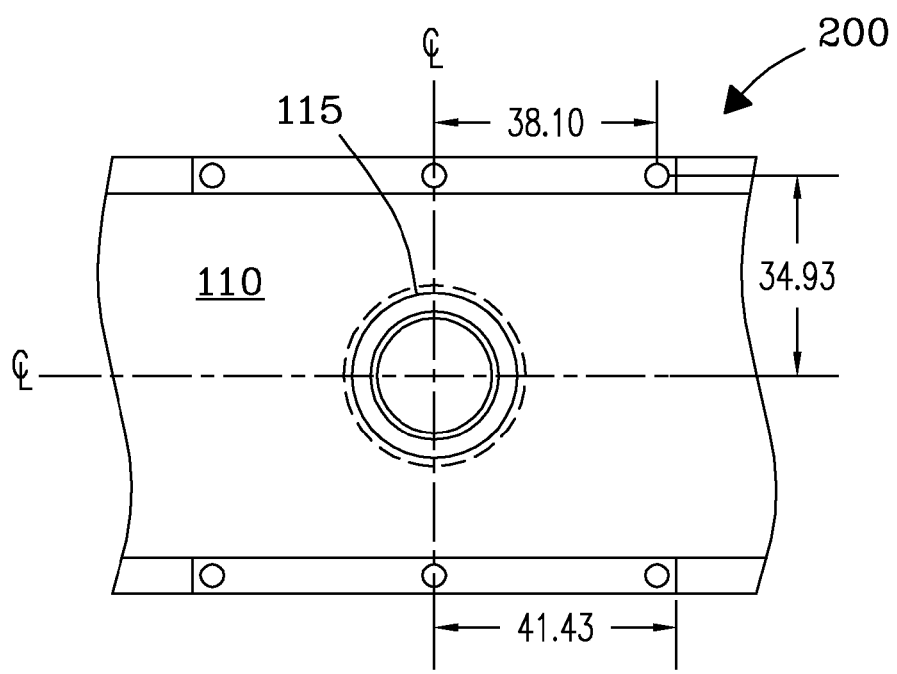
FIG. 2b shows a surface penetration through an external side wall of the optical device of FIG. 1 for introduction of source light.
Figure 2C:
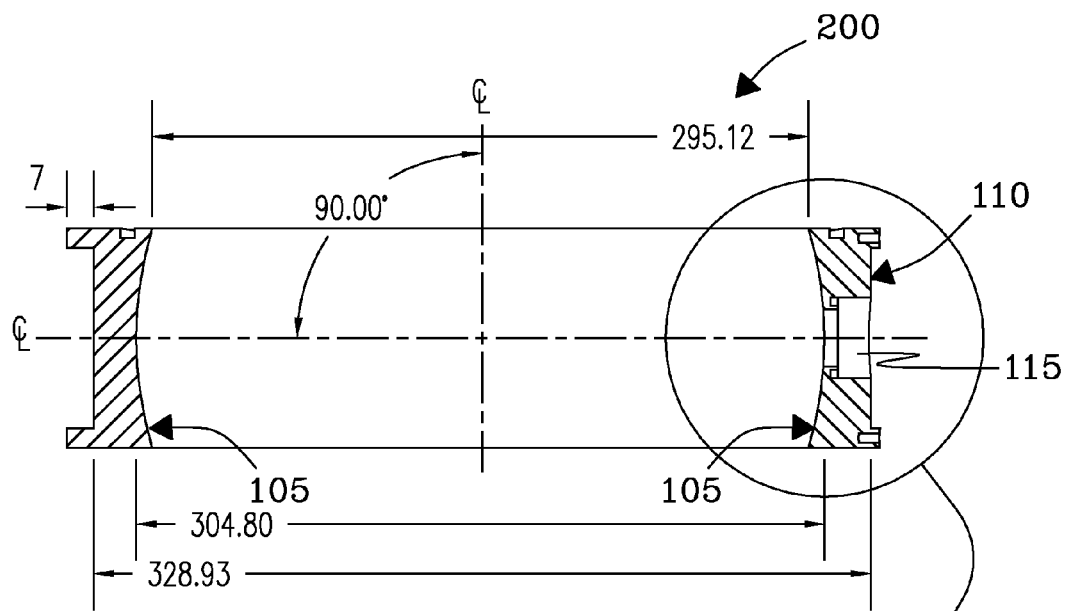
FIG. 2c shows a vertical cross section of the torus optical device of FIG. 1 through the surface penetration with exemplary dimensions.
Figure 2D:
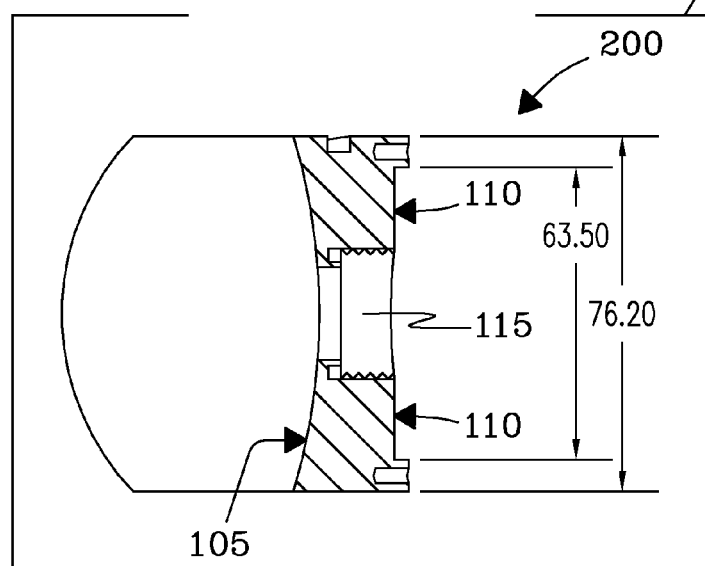
FIG. 2d shows an expanded vertical cross section of the torus optical device of FIG. 1 through the surface penetration with exemplary dimensions.
Figure 3:
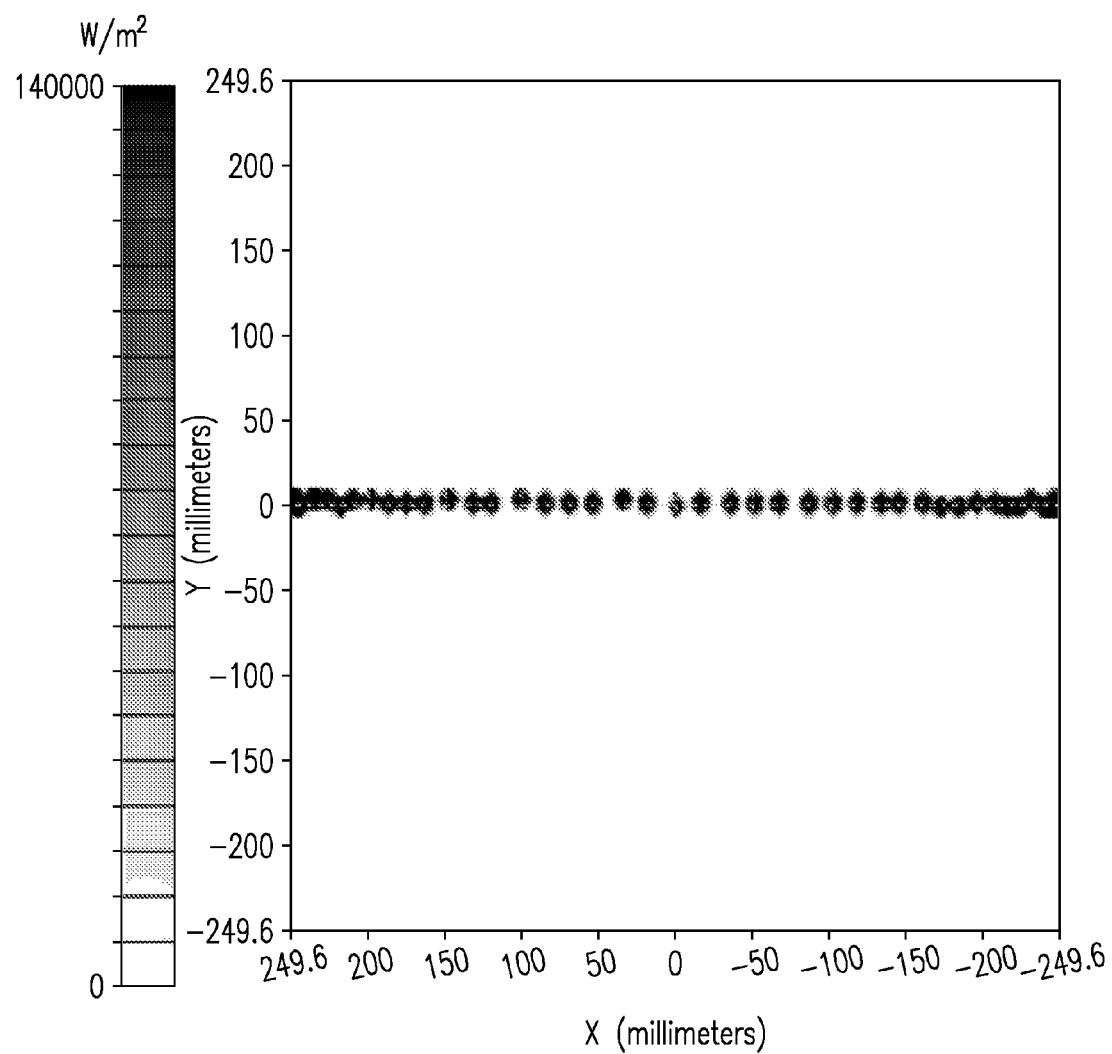
FIG. 3 shows the spot pattern resulting from projected light on the ring mirror of the optical device of FIG. 1.

FIGS. 2a-2d present schematics of torus optical device 200, configured with an open-air optical cavity 100, described previously herein in reference to FIG. 1, here shown with exemplary dimensions. FIG. 2a is an on-side view of the optical torus device 200. Exemplary dimensions are shown, but are not limited thereto. In the figure, the torus device includes an optical cavity 100, with a single interior ring mirror 105. The outer rim of the torus includes an external surface 110. FIG. 2b is a front view of optical device 200. The exterior surface 110 includes a surface penetration 115 or entry 115 for introduction of source (probe) light and extraction of absorption signal data. Exemplary dimensions are shown, but the optical device is not limited thereto. FIG. 2c is a vertical cross-sectional view of an external wall of optical device 200. In the figure, the mirror surface 105 is spherical (concave). External wall 110 includes a surface penetration 115 that penetrates the external wall and introduces source (probe) light into the optical cavity (not shown). Exemplary dimensions, including thickness of the external wall of the optical device, are shown, but dimensions of the optical device are not limited thereto. FIG. 2d is an expanded vertical cross-sectional view of an external wall of optical device 200. Mirror surface 105 is spherical (concave). External wall 110 includes a surface penetration 115 (launch hole) that penetrates the external wall and permits source (probe) light to be introduced into the optical cavity (not shown). Exemplary dimensions, including radial (i.e., curvature) dimensions of the mirror surface and height of the external wall, are shown, but dimensions of the optical device are not limited thereto. For example, height of the wall of the optical device can be preselected to reduce wall effects and to allow for modular design. For example, optical devices of the instant invention can be constructed, e.g., as modular units in which different lasers can be mounted to individual optical cells for detecting distinct chemical species. Alternatively, individual optical cells can be mounted in a stacked device configuration for detection of various gases, gas-phase analytes, or distinct chemical species of interest using preselected wavelengths of light. In this configuration, spare optical devices can permit rapid field maintenance by simply unbolting a suspect cell and replacing it with a spare. Further, the ring form-factor of the torus optical devices lends itself to direct attachment to vents and stacks for real-time gas monitoring in industrial applications. FIG. 3 shows the spot patterns that result from the projection of light on the spherical (concave) ring mirror of the optical device of FIG. 2a. In the figure, dimensions of the spot patterns (in millimeters) in the X-axis and Y-axis, respectively, and the intensity ($W/m^2$) of light in the cavity are shown. Height and length of the observed light pattern are a result of the choice of mirror surface and the selected curvature of the surface. In a typical experiment or analysis, the maximum number of roundtrips for light in the optical cavity is sought that achieves the maximum number of spots on the mirror surface before the light exits the torus, with minimal overlap in the propagation path. In the figure, the light pattern exhibits little or no spot overlap. Thus, a maximum number of round trips in the optical cavity is achieved, which maximizes path length and coverage of the mirror surface.

Single Ring Torus Design with Astigmatic Mirror

Figure 4:
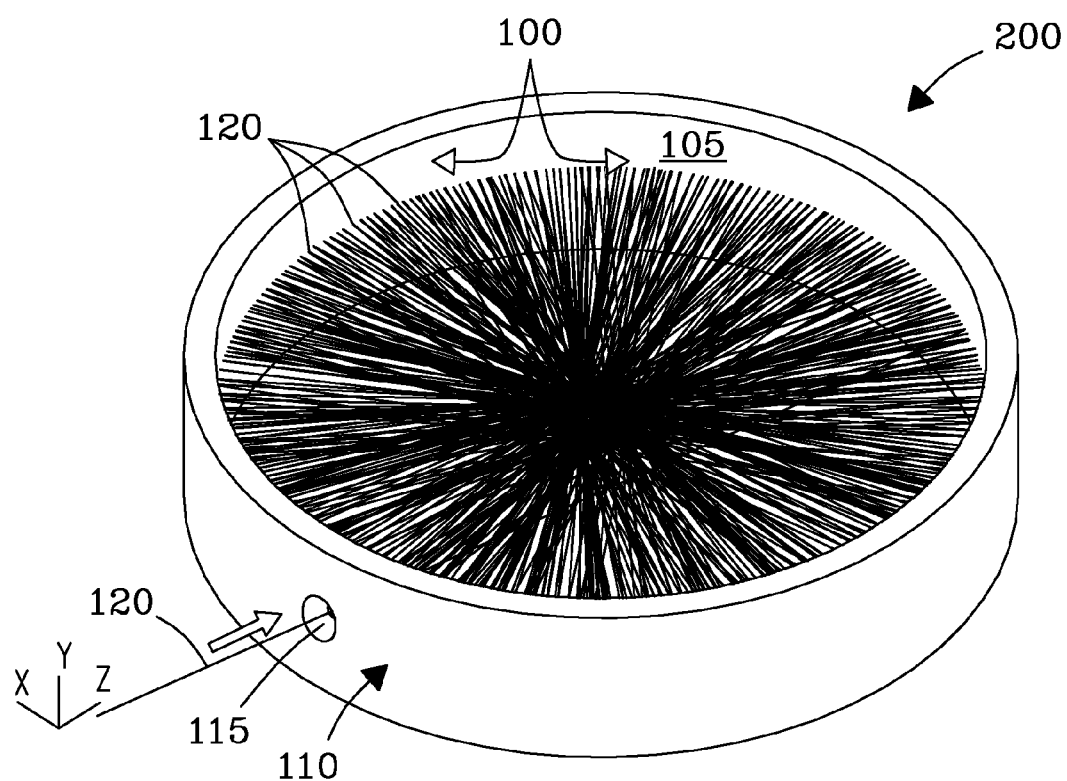
FIG. 4 illustrates a torus multipass optical device configured with a single astigmatic ring mirror, according to another embodiment of the invention.
Figure 5:
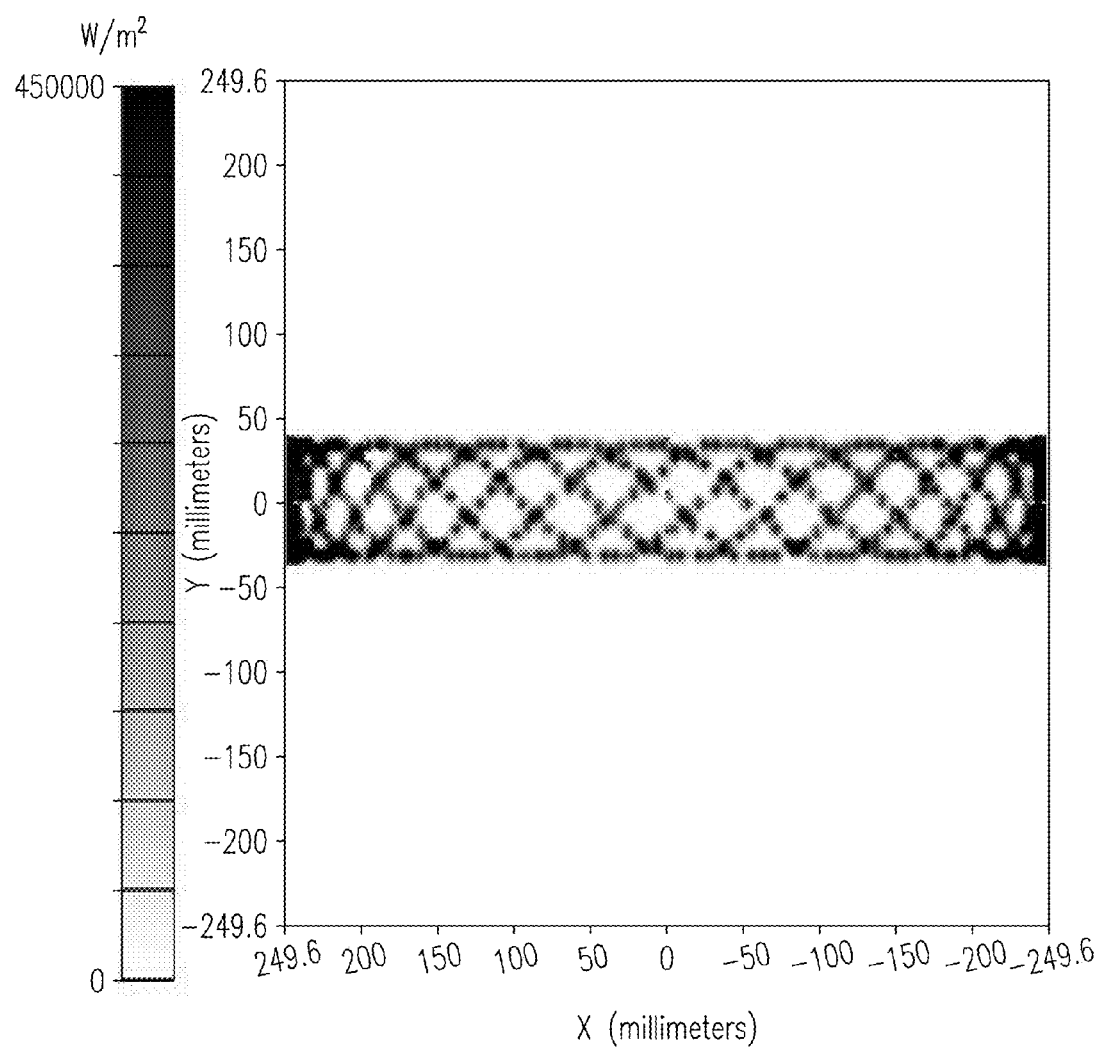
FIG. 5 shows the spot pattern resulting from projected light on the ring mirror wall of the optical device of FIG. 4.

FIG. 4 illustrates a torus multipass optical device 200 configured with a single astigmatic mirror, according to another embodiment of the invention. In the figure, device 200 includes an optical cavity 100 with a torus cross section. Optical cavity 100 is bounded by a single ring mirror 105, but is not limited thereto. In the instant device, the mirror is astigmatic, but is not limited thereto. Light (probe light) rays 120 are introduced to the optical cavity from a light source, e.g., a laser source (not shown), through a penetration (entry) 115 on exterior surface 110 and into the optical cavity. In the figure, a single penetration is shown at the center of external surface 110, but number and position of penetrations are not limited. Rays of light circulate within the annulus formed by the mirror surface of the inner torus ring. The astigmatic mirror causes light rays to fill more of the mirror surface which yields a greater path length than is achieved with a spherical surface. The astigmatic mirror delivers power (optical focusing) in two directions, both in the radial and in the axial direction. The instant device includes an open-air optical cavity 100, but is not limited thereto, as described previously herein. FIG. 5 shows exemplary spot patterns resulting from the projection of light on the ring mirror of the optical device of FIG. 4. In the figure, dimensions of the spot patterns (in millimeters) and the intensity (W/m$^2$) of light in the cavity are shown. A particular Lissajous pattern is traced out along the ring mirror of the torus optical device (cell) as a consequence of the selected launch angle of the light beam with respect to the X-axis, the Y-axis, or the combination of X-axis and Y-axis. The complex spot pattern is enabled by the astigmatic optics of the torus device, which causes light rays to fill more of the mirror surface that enables long path lengths in a small instrument volume. In an exemplary device, the torus is configured with an astigmatic mirror formed by revolving a mirror with 0.5 m radius of curvature about a 0.25 m radius. Dimensions are not limited. For example, the radius of the torus ring can be maintained, e.g., at 0.25 m (or increased or decreased), but is not limited thereto. In addition, the mirror radius in the axis orthogonal to the rotation axis (axial direction) can be maintained, decreased, or increased, e.g., to 0.5 m, but again is not limited. Other dimensions are suitable. In an exemplary test, light rays introduced into the optical cavity using an exemplary set of launch angles (e.g., 4 degrees and 10 degrees with respect to the X- and Y-axes, respectively), traverse the cell 1180 times, giving an approximate path length of 590 m in a volume of 0.02 m$^3$. If the launch angle with respect to the Y-axis causes the angle of incidence with respect to the mirror surface to exceed a certain threshold value, extremely large path lengths are possible in a small volume.

Dual Ring Torus Design with Spherical Mirror Surfaces

Figure 6:
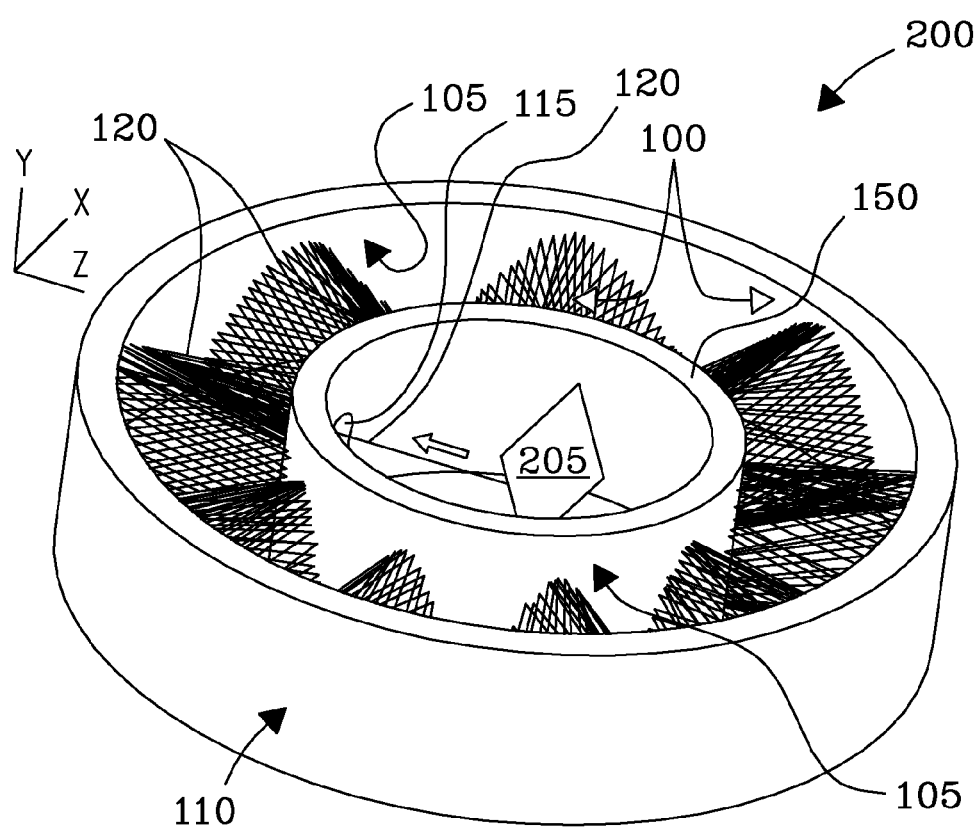
FIG. 6 illustrates a torus multipass optical device configured with dual ring mirrors and a central hub, according to yet another embodiment of the invention.
Figure 7:
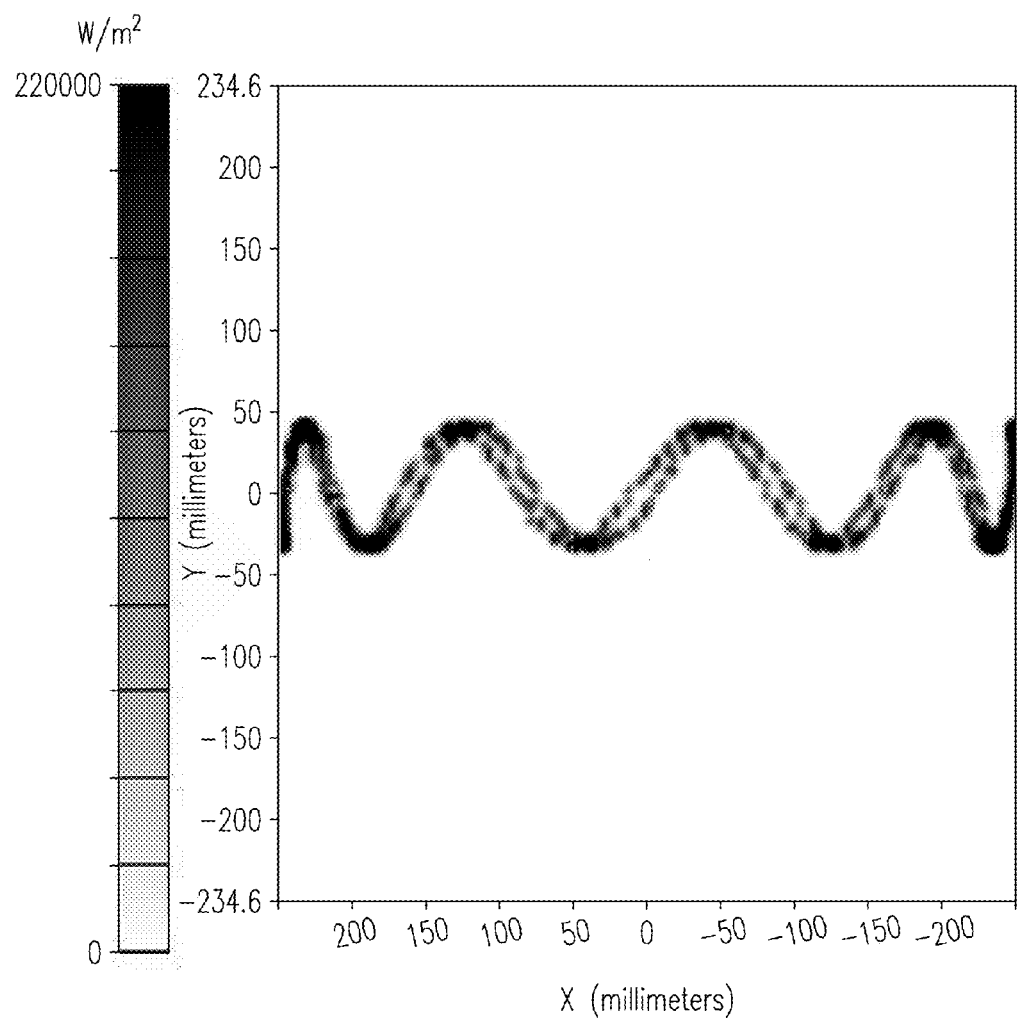
FIG. 7 shows the spot pattern resulting from projected light on the ring mirror wall of the optical device of FIG. 6.

FIG. 6 illustrates a torus multipass optical device 200 of a dual ring mirror design, according to yet another embodiment of the invention. In the figure, device 200 includes an optical cavity 100 defined by two ring mirrors 105 in a torus configuration. In the optical cavity, first (inner) ring mirror 105 surrounds a hub 150. The hub is located external to the inner ring mirror of the optical cavity at the center of the torus structure. The central hub is an open-air space located at the center of the forms that can be used to launch, distribute, divert, and dispense probe light into the optical cavity and receive and extract a return absorption signal and data from the optical cavity. A second (outer) ring mirror 105 defines the outer dimensions of the optical device and includes external surface 110. The optical (mirror) surfaces of the outer and the inner mirror face each other in the optical cavity. In the instant device, ring mirrors 105 are rotationally-symmetrically spherical (i.e., concave and/or convex) mirrors, but are not limited thereto. For example, mirror surfaces can each be symmetrically spherical in the radial and axial directions, i.e., concave, convex, or combinations of the two types, can be aspherical, or can include partially astigmatic optics, or can be fully astigmatic. In one configuration, the outer ring mirror surface along the axis of rotation (X-axis) in the radial direction and the axis (Z-axis) in the axial direction are concave; the inner ring mirror surface is necessarily convex in the radial direction but can be either convex or concave in the axial direction. In the figure, a light source 205, e.g., a quantum cascade laser (Hamamatsu Corp., Bridgewater, N.J.; Alpes Lasers SA, Neuchatel, Switzerland; or Maxion Technologies, Inc., College Park, Md.) or a tunable quantum cascade laser (Daylight Solutions, Inc., Poway, Calif.) is shown positioned within the central hub of the torus device for introducing light 120, e.g., a light beam or ray, into optical cavity 100. While a single instrument component, i.e., a light source, is shown coupled to the instant device, device components are not limited. For example, other instrument and allied components (e.g., beam optics, power supplies, detectors, amplifiers, etc.) can be utilized with the invention, e.g., as described further herein. No limitations are intended. Light (probe light) is launched from within central hub 150 through a penetration (opening) 115 into optical cavity 100, but is not limited thereto. While one surface penetration is shown and described here, number and location is not limited. Light can also be introduced through one or more penetrations in exterior wall 110 through the outer ring to the optical cavity, as described previously herein. No limitations are intended. All surface penetration locations and numbers of penetrations as will be contemplated by those of skill in the art are within the scope of the invention. Light 120 introduced to the cavity traverses a multipass optical path that generates a light pattern on the ring mirrors in the cavity. In the instant device, topology of a concave-convex resonator configuration is stable, but its waist lies outside the optical cavity. The term "waist" refers to the space or volume where the curvature of a Gaussian light beam is zero and has a width or diameter that is at a minimum. As such, ability to mode-match to the optical cavity can be more difficult. "Mode-matching" refers to the selection of light beam mode parameters (e.g., waist size) that match to mode parameters (e.g., radius of curvature of the mirrors) of the optical cavity. Mode-matching positions a stable light ray and path within the optical cavity. For example, light introduced into the optical cavity of the torus devices is preferably converging with the waist of the beam located at a position between the two mirror surfaces. For example, to launch light into the cavity with characteristics that match a stable mode of the cavity, light must converge with the waist of the beam located at a position between the two mirror surfaces. In another configuration, the axis (Y-axis) orthogonal to the axis of generation (Z-axis), includes two concave surfaces. Here, the waist lies between the two mirrors, thus the device is more easily mode-matched. In an exemplary configuration, device 200 has mirror radii of 500 mm along the X-axis (radial direction), and 250 mm (concave) and 125 nm (convex) in the Y-axis (axial direction). In this case, radius of curvature in the radial direction is negative, but in the axial direction, the torus optical device exhibits positive power (concave surface profile). It is also possible to construct the ring mirrors that have negative radii of curvature (negative power) in both the radial and axial (orthogonal) directions (i.e., convex surface profiles). In one exemplary configuration, for example, the inner ring mirror can be constructed with a radius of curvature that is negative (convex surface profile) in both the radial and axial (orthogonal) directions which delivers a negative power. By necessity, the radius of curvature in the radial direction must be negative, and in the axial direction, the construction yields a negative power. No limitations are intended. All mirror surfaces as will be contemplated by those of skill in the art in view of the disclosure are within the scope of the invention. The torus configured with dual rings can be enclosed, sealed, and evacuated for trace-level determination of gases and gas-phase analytes, as described further herein. In one exemplary dual ring configuration, in which the inner ring mirror surface has a convex-concave profile in the axial and radial directions, respectively, gases and gas-phase analytes circulate within the annular space of optical cavity 100, between hub 150 and outer rim 110, and are analyzed using light rays that also traverse the annulus of the optical cavity. FIG. 7 shows an exemplary spot pattern resulting from the projection of light on the ring mirrors of the optical device of FIG. 6. In the figure, dimensions of the spot patterns (in millimeters) and the intensity (W/m$^2$) of light in the cavity are shown. Light rays introduced to the optical cavity trace out a pattern around the circumference of the optical cavity of the torus that propagate in the both radial and the axial direction. As shown in the figure, the light pattern is sinusoidal, but is not limited thereto.

Construction of the Multipass Optical Device

The torus multipass optical device of the invention is constructed of materials including, but not limited to, e.g., metals, ceramics (e.g., AlOx, silicon carbide, tungsten carbide), glasses (e.g., silicate glasses, oxide glasses, fluoride glasses), and combinations of these materials. The torus structure (torus) of the optical device is preferably monolithic to minimize seams or interfaces in the optical cavity. Machining of the torus is preferably done using a diamond turning process or other deterministic fabrication process to minimize aberrations in the optical surfaces. For a selected ring mirror, a radius of curvature can be introduced that delivers a path length that achieves a desired signal-to-noise result for determination of gases and gas-phase analytes. Signal-to-noise obtained for an analysis is a function of the absorption characteristics of each gas or gas-phase analyte, laser power, mirror reflectivity, and detector shot noise limit. Mirroring of the optical surfaces of the torus is preferably accomplished using an electroplating, or other suitable surface mirroring, process that provides desired optical properties at the mirror surfaces. All dimensions for the torus optical device as will be implemented by those of skill in the optical arts that provide desired properties for gas and analyte determination at selected detection limits are within the scope of the invention. No limitations are intended by the descriptions to exemplary dimensions and embodiments.

Exemplary System Configurations

Figure 8:
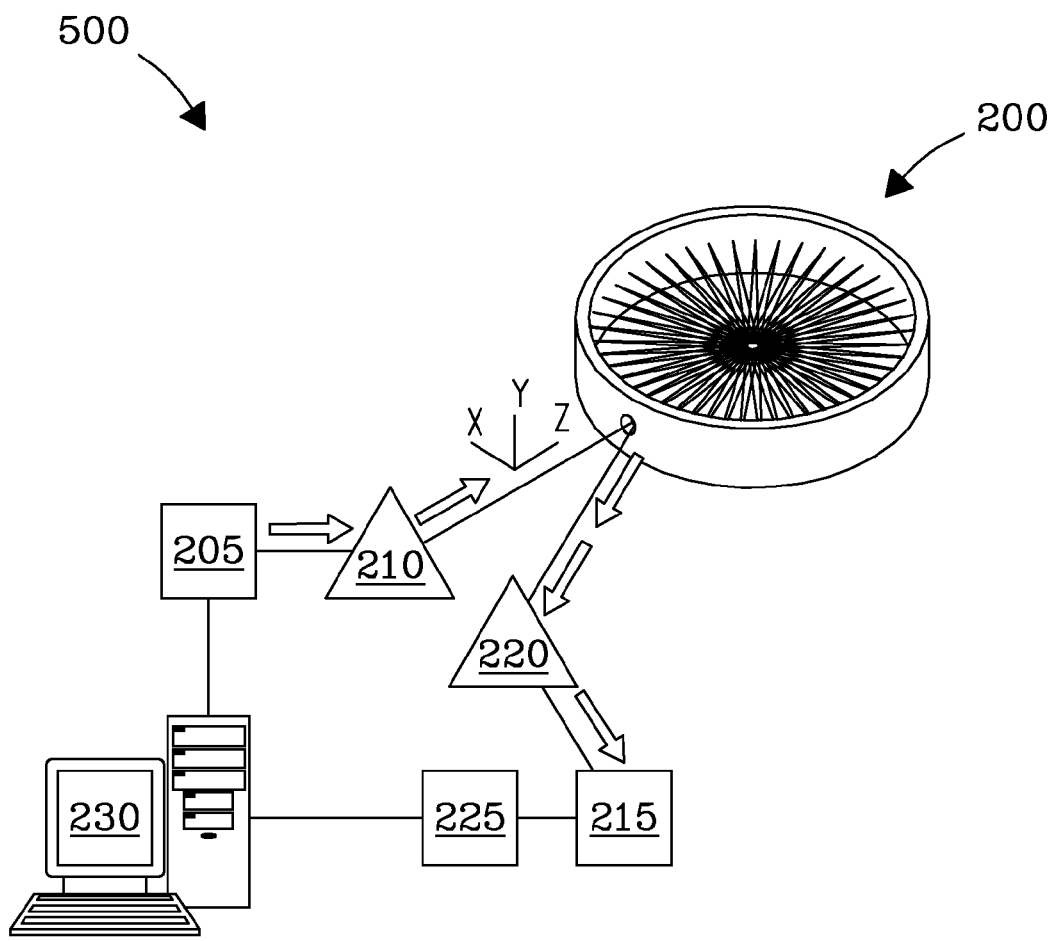
FIG. 8 shows a gas absorption analysis system that includes a torus multipass optical device of an open-air design, according to an embodiment of the invention.
Figure 9:
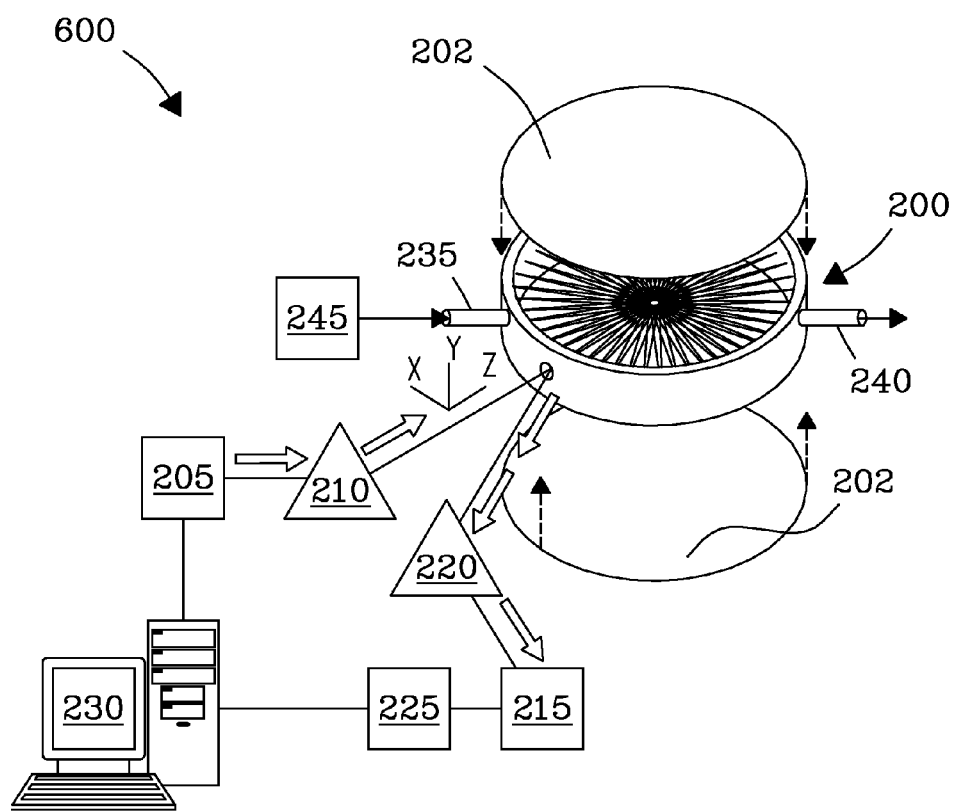
FIG. 9 shows a gas absorption analysis system that includes a torus multipass optical device with a sealed optical cavity, according to another embodiment of the invention.
Figure 10A:
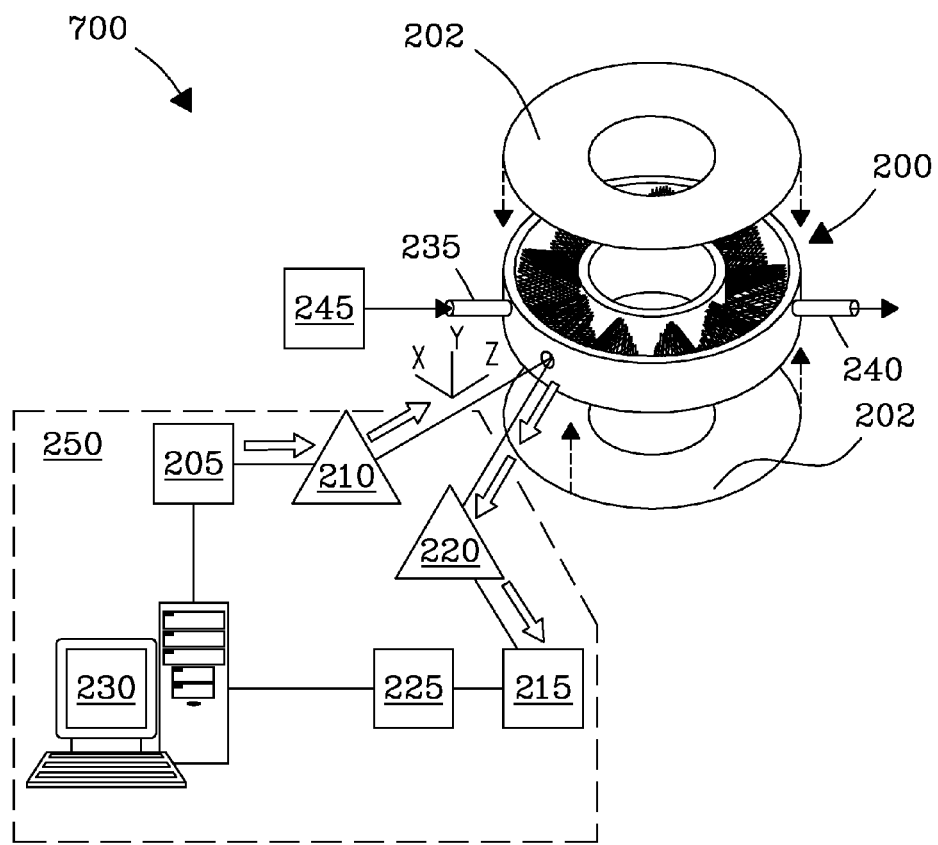
FIG. 10a shows a gas absorption analysis system that includes a torus multipass optical device of a dual ring design and a central hub and a sealed optical cavity, according to yet another embodiment of the invention.
Figure 10B:
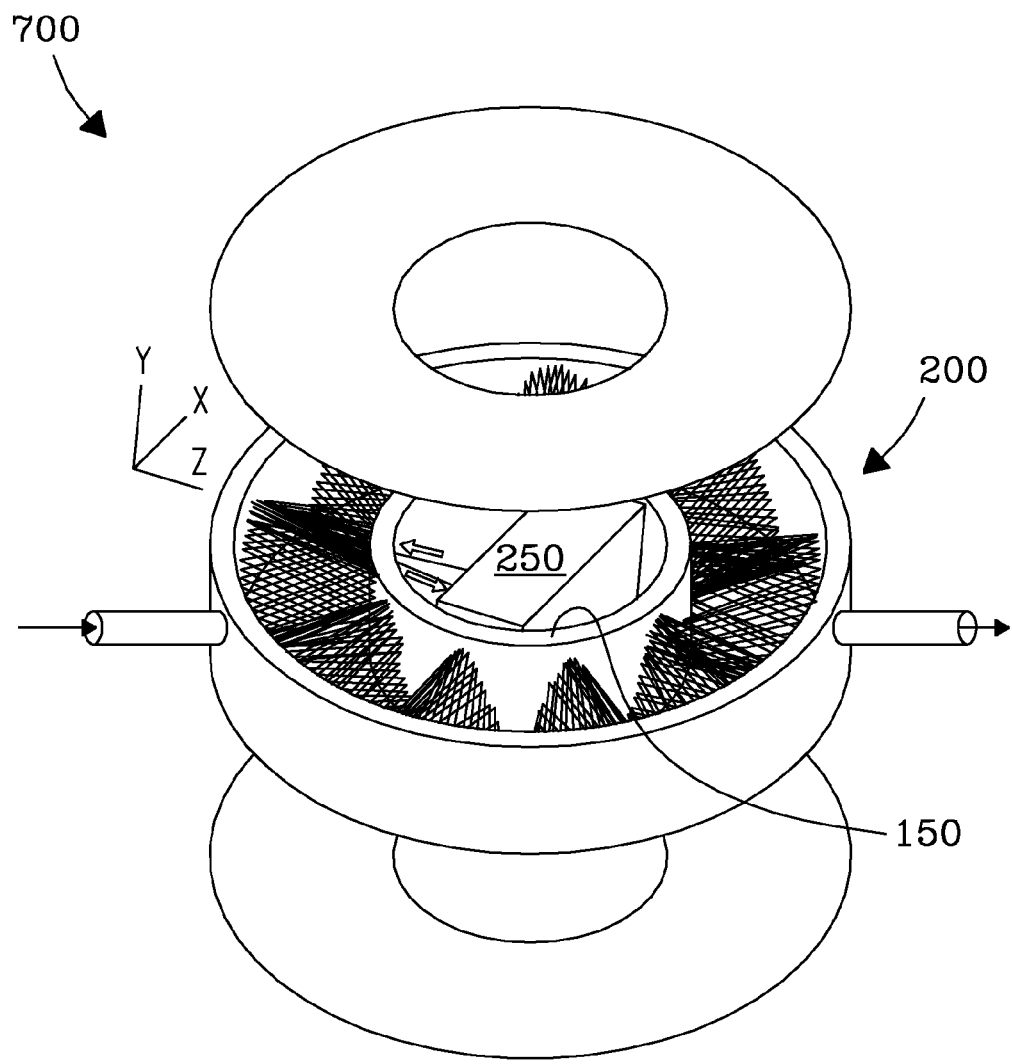
FIG. 10b shows a gas absorption analysis system that includes a torus multipass optical device of a dual ring design and a central hub configured with probe light and detection components within the central hub, according to still yet another embodiment of the invention.

FIG. 8 shows an exemplary analysis system 500 that includes a torus multipass optical device 200, according to an embodiment of the invention. System 500 provides for determination of gases and gas-phase analytes. Components of the system include, but are not limited to, a light source 205, e.g., a quantum cascade laser (Hamamatsu Corp., Bridgewater, N.J.; Alpes Lasers SA, Neuchatel, Switzerland; or Maxion Technologies, Inc., College Park, Md.) or a tunable quantum cascade laser (Daylight Solutions, Inc., Poway, Calif.); beam steering, focusing, and mode-matching optics 210 including, e.g., plane mirrors and lenses; electronics components (e.g., laser power supply, modulation source) for light source (e.g., laser) modulation and detection (not shown); an optical detector 215, e.g., a thermo-electrically cooled HgCdTe detector (Hamamatsu Hamamatsu Corp., Bridgewater, N.J.); detection optics 220 including, e.g., plate beam splitters and detector lens; a lock-in amplifier 225, e.g., a phase-sensitive or lock-in amplifier (Stanford Research Systems, Sunnyvale Calif.); and one or more computers 230 that provide control of, e.g., introduction of light from the light source to the optical cavity, light source (laser) modulation and detection electronics, recording and analysis of optical data (e.g., wavelength and absorption data), and other analysis components or processes. In the figure, system components and equipment are positioned external to the optical cavity near the exterior wall of the torus, but is not limited thereto. In the instant configuration, probe light is launched from a light source into the optical cavity through an opening (entry hole or penetration) in the exterior surface of the torus optical device. The light or absorption signal returning through the opening is extracted, measured, and analyzed to determine the gas or gas-phase analyte. FIG. 9 shows another analysis system 600 that includes a torus multipass optical device 200 with a sealed optical cavity configured with a single ring mirror described previously herein (FIG. 1 and FIG. 4), according to another embodiment of the invention. System 600 provides for determination of gases and gas-phase analytes. Optical device 200 can be sealed, e.g., with cover plates 202 (e.g., metal plates) that enclose the optical cavity. The system further includes, but is not limited to, a suitable light source 205, e.g., a quantum cascade laser (Hamamatsu Corp., Bridgewater, N.J.; Alpes Lasers SA, Neuchatel, Switzerland; or Maxion Technologies, Inc., College Park, Md.) or a tunable quantum cascade laser (Daylight Solutions, Inc., Poway, Calif.); beam steering, focusing, and mode-matching optics 210 including, e.g., plane mirrors and lenses; electronics components (e.g., laser power supply, modulation source) for light source (e.g., laser) modulation and detection (not shown); an optical detector 215, e.g., a thermo-electrically cooled HgCdTe detector (Hamamatsu Hamamatsu Corp., Bridgewater, N.J.); detection optics 220 including, e.g., plate beam splitters and detector lens; a lock-in amplifier 225, e.g., a phase-sensitive or lock-in amplifier (Stanford Research Systems, Sunnyvale Calif.); and one or more computers 230 that provide control of, e.g., introduction of light from the light source to the optical cavity, light source (laser) modulation and detection electronics, recording and analysis of optical data (e.g., wavelength and absorption data), and other analysis components or processes. In the figure, inlet line 235 provides for introduction of gases and gas-phase analytes into the optical cavity for analysis. Output line 240 provides for removal of gases and analytes from within the optical cavity following analysis. A source of purge gas (e.g., $N_2$ gas) 245 can also be coupled to the optical device to sweep gases and analytes from the optical cavity between measurements. Pumps and pumping components (not shown) may also be coupled to reduce pressure within, or to evacuate, the optical cavity. In the figure, system components and equipment are positioned external to the optical cavity adjacent to the exterior wall of the torus, but is not limited thereto. In the instant configuration, probe light is launched from the light source into the optical cavity through an opening (entry hole or wall penetration) in the exterior surface of the torus. The light or absorption signal returning through the opening is extracted, measured, and analyzed to determine the gas or gas-phase analyte. FIG. 10a shows yet another analysis system 700 for determination of trace gases and trace gas-phase analytes that includes a torus multipass optical device 200 with an optical cavity that is sealed, configured with dual ring mirrors and a central hub external to the optical cavity described previously herein (FIG. 6), according to another embodiment of the invention. Cover plates 202 (e.g., metal plates) enclose and seal the optical cavity. In the figure, a set 250 of system and instrument components is shown that are used to introduce probe light into the optical cavity and to detect the absorption signal returned from the optical cavity. A light source 205, e.g., a quantum cascade laser (Hamamatsu Corp., Bridgewater, N.J.; Alpes Lasers SA, Neuchatel, Switzerland; or Maxion Technologies, Inc., College Park, Md.) or a tunable quantum cascade laser (Daylight Solutions, Inc., Poway, Calif.) delivers light to subsequent beam steering, focusing, and mode-matching optics 210 (e.g., plane mirrors and lenses) where the laser probe light is, e.g., mode-matched and introduced into the optical cavity of torus optical device 200. Detection optics 220 (e.g., plate beam splitters and detector lenses) direct an absorption signal returning from the optical cavity to optical detector 215 (e.g., a thermo-electrically cooled HgCdTe detector, Hamamatsu Hamamatsu Corp., Bridgewater, N.J.) for detection. A lock-in amplifier (Stanford Research Systems, Sunnyvale Calif.) 225 or phase-sensitive detector can be coupled to extract the absorption signal from the returning light beam. One or more computers 230 provide control of, e.g., the power supply of the light source (laser), the light source that introduces light into the optical cavity, the modulation electronics that modulate probe light from the light source (e.g., laser), the detectors and detector electronics that detect the absorption signal in the returning light beam, and that further provide for recording and analysis of optical data (e.g., wavelength and absorption data). Other instrument and analysis components may also be interfaced and controlled via computer. No limitations are intended. In the figure, inlet 235 permits gases and gas-phase analytes to be introduced into the optical cavity for analysis. Output 240 permits gases and analytes to be removed from within the optical cavity following analysis. A source of purge gas (e.g., $N_2$ gas) 245 can also be coupled to the optical device to sweep gases and analytes from the optical cavity between measurements. Pumps and pumping components (not shown) may also be coupled to reduce pressure within, or to evacuate, the optical cavity as will be understood by those of skill in the art. In the figure, system components in set 250 are located outside of the optical cavity and outer ring mirror, but position is not limited thereto. FIG. 10b shows an alternate configuration for components of system 700. In the instant configuration, system and instrument components in set 250 used in conjunction with the torus optical device 200, can also be positioned within central hub 150, but illustrated components are not intended to be limiting. For example, one or more of the instrument components within set 250, e.g., a light source and a detector (FIG. 10a) may be alternatively installed within the central hub of the torus optical device, but is not limited thereto. In one configuration, probe light is launched from within the central hub through a penetration (opening) in the central hub wall and introduced into the optical cavity. In this configuration, the light or absorption signal can also be extracted, measured, and/or analyzed from within the central hub by positioning suitable instrument components (i.e., from set 250) therein. Signal analysis components may be co-located within the central hub or located external to the central hub and/or performed offline. No limitations are intended. The central hub allows more robust and compact packaging options, especially for airborne or environmentally-challenging applications. For example, detector optics can be housed within the central hub with the analyte circulating within the annular region of the optical cavity between the hub and outer rim. This configuration has a benefit especially useful in airborne applications where the optical device could be attached to an airframe or an emissions duct. Other systems, devices, configurations, and applications as will be considered or implemented by those of skill in the art in view of the disclosure are within the scope of the invention.

System Operation

Figure 11:
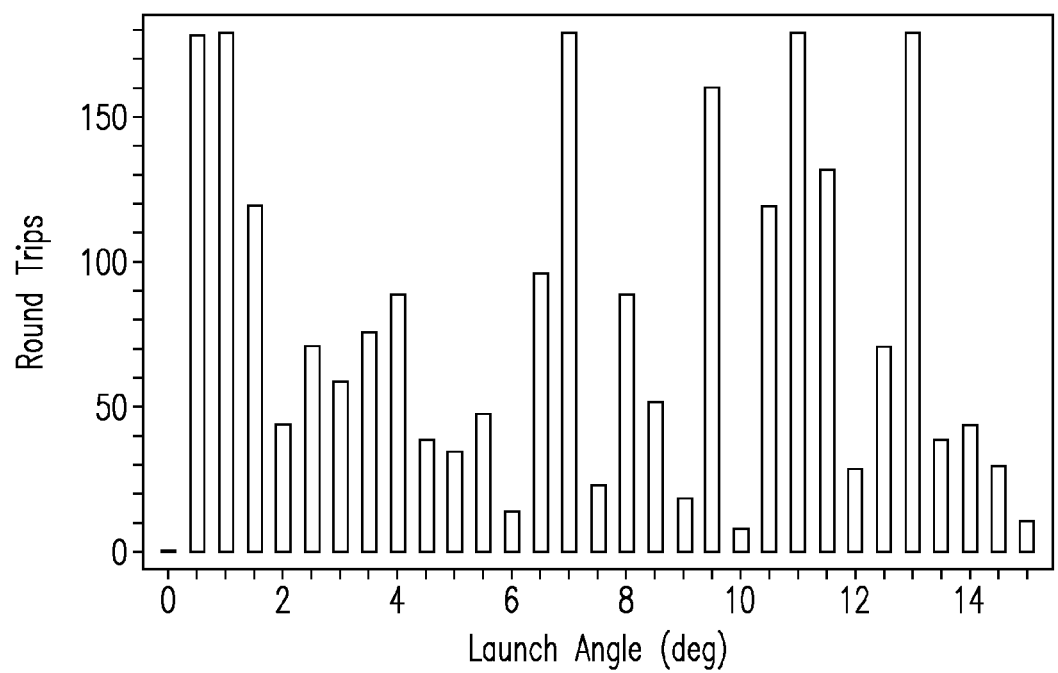
FIG. 11 plots the number of optical passes (roundtrips) within the optical cavity of a torus optical device as a function of the launch angle of initial light beam.

In the system described herein, the torus optical devices are of a compact and a monolithic construction that include shallow wall dimensions ideally suited for trace gas measurements in field, airborne, and planetary exploration environments. Operating conditions used for the torus multipass devices in their various systems are determined based on the detection goals desired for the instrument system. As is common for many kinds of instrumentation, the user must weigh instrumental sensitivity against cost and reliability concerns. FIG. 11 plots the number of optical passes (roundtrips) within the optical cavity of a spherical torus optical device as a function of the initial launch angle of the light beam. Here, number of round trip passes possible for a spherical ring torus optical device is shown as a function of initial beam launch angle for angles up to 15 degrees, calculated using TRACEPRO® software (Lambda Research, Corp., Littleton, Mass., USA). In the figure, for a 0.5 m diameter cell, 180 passes of light within the optical cavity will achieve a 90 m path length. Optical cross-sections for determination of species of interest can be identified, e.g., using molecular absorption databases such as, e.g., the High-Resolution Transmission Molecular Absorption (HITRAN) database available on the world-wide web at the FTP-site of the Smithsonian Astrophysical Observatory, Cambridge, USA. Software updates and corrections for this database are available at: http://cfa-www.harvard.edu/hitran//. An analogous database being developed at the Harvard-Smithsonian Center for Astrophysics (Atomic and Molecular Physics Division), the High-Temperature Spectroscopic Absorption Parameters (HITEMP) database, includes high-temperature spectroscopic absorption data and associated parameters. From these database sources, or other research publications, one determines the cross section of a desired molecule, analyte, or gas species of interest and then determines whether the path length attainable in the torus optical device is suitable for determination of the desired analyte at the desired detection limit or selected concentration. If not, then an alternate torus optical device or system configuration can be considered, e.g., a device with an astigmatic optical cavity (see FIG. 4). A non-sequential ray tracing program such as TRACEPRO can then be used to determine the expected number of round trips and thus path length as a function of beam launch angles. In operation, a tunable laser can be selected that tunes across a broad spectral region, e.g., where spectral absorption features of the selected species (e.g., gases or gas-phase analytes), or features of a majority of species, are expected. Alternatively, multiple disrupted feedback lasers can be used that tune in the molecular fingerprint region, or in the overtone region, of atmospheric molecules or analytes of interest. Direct absorption spectroscopy, in which the laser is tuned in wavelength while transmission of the beam through the multipass optical device is monitored is preferred. For weak signals or signals that are obscured due to collisional broadening, wavelength modulation spectroscopy combined with 2f detection can be employed, e.g., as described by J. T. C. Liu et al. (*Appl Phys. B.*, Vol. 78, 503-511 (2004)], which reference is incorporated herein. For example, in 2f spectroscopy, the laser is modulated with a small-signal sinusoidal modulation as its wavelength is slowly ramped across its scan range. A phase-sensitive detector can then be used to extract the absorption signal at an enhanced signal-to-noise value. Instrument and device configurations and processes described herein are not intended to be limited. All spectroscopic methods for gas and analyte determination, conducted in concert with ring torus multipass optical devices of the invention described herein, are within the scope of the invention. For example, while exemplary embodiments of the present invention have been shown and described, it will be apparent to those skilled in the art that many changes and modifications may be made without departing from the invention in its true scope and broader aspects.

I claim:
1. A multipass optical device, characterized by:
   a torus structure that defines an optical cavity that includes at least one seamless ring mirror with a surface of revolution along the circumference that is rotationally symmetric with no defined optical axis, said at least one ring mirror provides optical power that propagates light introduced to said cavity in at least a radial direction and an axial direction such that it is optically continuous at all locations on the face thereof, defining a multipass optical path of a predefined path length.

2. The optical device of claim 1, wherein said optical cavity includes a single ring mirror.

3. The optical device of claim 2, said single ring mirror has an optical surface selected from the group consisting of: spherical surfaces, concave spherical surfaces, convex spherical surfaces, equi-concave spherical surfaces, aspherical surfaces, astigmatic surfaces, and combinations thereof.

4. The optical device of claim 1, wherein said optical cavity includes two concentric ring mirrors each of which has an optical surface that faces, and is disposed apart from, the other in said cavity.

5. The optical device of claim 4, said device further includes a hub disposed at the center of said device external to said optical cavity.

6. The optical device of claim 4, said concentric ring mirrors each have an optical surface selected from the group consisting of: spherical surfaces, concave spherical surfaces, convex spherical surfaces, equi-concave spherical surfaces, aspherical surfaces, astigmatic surfaces, and combinations thereof.

7. The optical device of claim 6, wherein one of said concentric ring mirrors is a convex ring mirror and one of said ring mirrors is a concave ring mirror.

8. The optical device of claim 6, wherein at least one of said concentric ring mirrors is an astigmatic mirror or includes an astigmatic portion.

9. The optical device of claim 1, wherein said at least one ring mirror has a radius of curvature equal to the radius of revolution of said optical cavity.

10. The optical device of claim 1, wherein said at least one ring mirror has a radius of curvature different from the radius of revolution of said optical cavity.

11. The optical device of claim 1, wherein said optical cavity is an open-air cavity.

12. The optical device of claim 1, wherein said optical cavity is a sealed cavity.

13. The optical device of claim 12, wherein said sealed cavity is an evacuated sealed cavity.

14. The optical device of claim 12, wherein said sealed cavity is a partially evacuated sealed cavity with a reduced pressure atmosphere.

15. The optical device of claim 1, said device includes at least one surface opening that allows light to enter into, and exit from, said optical cavity.

16. The optical device of claim 15, wherein said at least one opening is an off-center axis opening.

17. The optical device of claim 15, wherein said at least one opening is an on-center axis opening.

18. The optical device of claim 15, wherein said at least one opening is an opening through an external surface within said central hub.

19. The optical device of claim 1, wherein said multipass optical path includes a path length predefined in the range from about 10 meters to greater than or equal to 1000 meters.

20. A method for determination of a gas or a gas-phase analyte, comprising:
   introducing a gas or a gas-phase analyte into an optical device comprising a torus structure that defines an optical cavity that includes at least one seamless ring mirror with a surface of revolution along the circumference that is rotationally symmetric with no defined optical axis, said at least one ring mirror provides optical power that propagates light introduced to said cavity in at least a radial direction and an axial direction such that it is optically continuous at all locations on the face thereof, defining a multipass optical path of a predefined path length;
   introducing light into said optical cavity at a preselected launch angle and preselected wavelength, said gas or said gas-phase analyte absorbs light at a wavelength characteristic for said gas or said gas-phase analyte;
   measuring an absorption signal for said gas or said gas-phase analyte; and
   determining said gas or said gas-phase analyte.

21. The method of claim 20, wherein the step of introducing said gas or said gas-phase analyte includes an optical cavity with two concentric ring mirrors, each of said mirrors has an optical surface selected from the group consisting of: spherical surfaces, concave spherical surfaces, convex spherical surfaces, equi-concave spherical surfaces, aspherical surfaces, astigmatic surfaces, and combinations thereof.

22. The method of claim 21, wherein the step of introducing a gas or a gas-phase analyte includes an optical cavity with at least one convex ring mirror or at least one concave ring mirror.

23. The method of claim 21, wherein the step of introducing a gas or a gas-phase analyte includes use of an optical cavity with an astigmatic mirror or an astigmatic mirror portion.

24. The method of claim 20, wherein the step of introducing a gas or a gas-phase analyte includes use of an optical cavity with at least one ring mirror that has a radius of curvature equal to the radius of revolution of said optical cavity.

25. The method of claim 20, wherein the step of introducing a gas or a gas-phase analyte includes use of an optical cavity with at least one ring mirror that has a radius of curvature different from the radius of revolution of said optical cavity.

26. The method of claim 20, wherein the step of introducing a gas or a gas-phase analyte includes partially evacuating said optical cavity prior to introducing said gas or said gas-phase analyte.

27. The method of claim 20, wherein the step of introducing a gas or a gas-phase analyte includes evacuating said optical cavity prior to introducing said gas or said gas-phase analyte.

28. The method of claim 20, wherein the step of introducing light into said optical cavity includes light of a preselected wavelength.

29. The method of claim 20, wherein the step of introducing light into said optical cavity includes a launch angle with respect to X- or Y-axes selected in the range from about 1 degree to about 50 degrees, respectively.

30. The method of claim 20, wherein the step of introducing light includes use of an optical cavity that is open to air.

31. The method of claim 20, wherein said optical device is used as a component of a gas detection system or instrument.

32. The method of claim 20, wherein said optical device is used as an absorption device for spectroscopy of a gas or a gas-phase analyte.

33. The method of claim 20, wherein said optical device is used as an emission stack monitor for real-time measurement of effluent gases.

34. The method of claim 20, wherein said optical device is used as a modular element or component in a multi-wavelength absorption spectroscopy system or process.

35. The method of claim 20, wherein said optical device is used as a gas sensor in an airborne gas measurement device or process.

36. The method of claim 20, wherein said optical device is used to determine a gas or a mixture of gases.

37. The method of claim 20, wherein said optical device is used as a component of a gas-phase analyte detection system or process.

38. The method of claim 20, wherein said device is used in a stack comprising two or more of same for determination of two or more preselected gases or gas-phase analytes.

39. In a system, a torus multipass optical device, comprising:

a torus structure that defines an optical cavity that includes at least one seamless ring mirror with a surface of revolution along the circumference that is rotationally symmetric with no defined optical axis, said at least one ring mirror provides optical power that propagates light introduced to said cavity in at least a radial direction and an axial direction such that it is optically continuous at all locations on the face thereof, defining a multipass optical path of a predefined path length.

40. The system of claim 39, further including a laser light source.

41. The system of claim 39, further including beam steering, focusing, and mode-matching optics.

42. The system of claim 39, further including an optical detector.

43. The system of claim 39, further including a lock-in detector.

* * * * *

UNITED STATES PATENT AND TRADEMARK OFFICE
CERTIFICATE OF CORRECTION

| | | |
|---|---|---|
| PATENT NO. | : 7,876,443 B2 | Page 1 of 1 |
| APPLICATION NO. | : 12/239978 | |
| DATED | : January 25, 2011 | |
| INVENTOR(S) | : Bruce E. Bernacki | |

It is certified that error appears in the above-identified patent and that said Letters Patent is hereby corrected as shown below:

Col. 7, line 67: after 115, insert --(launch hole)--

Col. 9, line 39: replace "forms" with "torus"

Signed and Sealed this

Seventh Day of August, 2012

David J. Kappos
*Director of the United States Patent and Trademark Office*